(12) United States Patent
Siegel et al.

(10) Patent No.: US 11,802,117 B2
(45) Date of Patent: Oct. 31, 2023

(54) CONVERSION OF CBD TO D8-THC TO D6A10A-THC

(71) Applicants: Alexander William Siegel, Albany, CA (US); Alek Enrique Valle, Novato, CA (US); Devin Jay Wall, Vallejo, CA (US)

(72) Inventors: Alexander William Siegel, Albany, CA (US); Alek Enrique Valle, Novato, CA (US); Devin Jay Wall, Vallejo, CA (US)

( * ) Notice: Subject to any disclaimer, the term of this patent is extended or adjusted under 35 U.S.C. 154(b) by 0 days.

(21) Appl. No.: 17/458,130

(22) Filed: Aug. 26, 2021

(65) Prior Publication Data
US 2023/0064132 A1     Mar. 2, 2023

(51) Int. Cl.
*C07D 311/80*     (2006.01)

(52) U.S. Cl.
CPC .................................. *C07D 311/80* (2013.01)

(58) Field of Classification Search
None
See application file for complete search history.

(56) References Cited

PUBLICATIONS

Srebnik et al. (Journal of the Chemical Society Perkin Transactions 1984, 2881-2886).*

* cited by examiner

*Primary Examiner* — Samantha L Shterengarts
(74) *Attorney, Agent, or Firm* — Brubaker Law Group PLLC

(57) ABSTRACT

Methods of converting CBD to Δ8-THC to Δ10-THC to Δ6a10a-THC are described and the products disclosed. Various adjustments can be made to the reactions resulting in increased or decreased product and by-product.

20 Claims, 2 Drawing Sheets

CONVERSION OF CBD TO D8-THC TO D6A10A-THC

TECHNICAL FIELD

The present invention relates to the chemical synthesis of an extract of hemp. More specifically, the present invention relates to converting CBD and further Δ8-THC into Δ6a10a-THC, sometimes with a minor product of Δ9-THC, Δ10-THC, and CBN.

BACKGROUND

Public interest in *Cannabis* as medicine is well-established based in no small part on the fact that *Cannabis* has long been considered to have medicinal properties, ranging from treatment of cramps, migraines, convulsions, appetite stimulation and attenuation of nausea and vomiting. In fact, a report issued by the National Academy of Sciences' Institute of Medicine indicated that the active components of *Cannabis* appear to be useful in treating pain, nausea, AIDS-related weight loss, muscle spasms in multiple sclerosis as well as other problems. Advocates of medical marijuana argue that it is also useful for glaucoma, Parkinson's disease, Huntington's disease, migraines, epilepsy and Alzheimer's disease.

Δ8-THC: Is a common synthetic THC obtained through acidic reactions with either cannabidiol (CBD) or Δ9-THC. Δ8-THC is psychoactive and is reported to have around 50% to 66% of the activity of Δ9-THC.

Δ10-THC: Prior art reports the synthesis of the two stereoisomers obtained by base catalyzed isomerization of (−)-trans-Δ9-THC by Srebnik in 1984. Treatment of (−)-trans-Δ9-THC with base gave a mixture of (6aR-trans)-Δ10-THC (m.p. 153-154° C.; α −133°) and (6aR-cis)-Δ10-THC (m.p. 54-55° C.; α −70°), that are further separated by chromatography. Δ10-THC has no reported psychoactivity, is stable in solution, and may be a viable non-psychoactive therapeutic compound. Δ10-THC may be a viable "cutting" agent, which can thicken and dilute *cannabis* or hemp extract without adding psychoactivity or other physical effects. Use of Δ10-THC as a cutting agent for CBD products may also be viable as Δ10-THC is not currently identified by any known state or federal testing hemp laboratory.

Δ6a10a-THC: Δ6a10a-THC is not a naturally occurring cannabinoid and is generally obtained by chemical synthesis. The condensation between olivetol and pulegone under acid catalysis for the preparation of Δ6a10a-THC in its racemic form was investigated in the early 1940s. The synthesis and isolation of (R)-(+)-Δ6a10a-THC and (S)-(−)-Δ6a10a-THC was achieved in 1984. The method used the single enantiomers of Δ10-THC1, (9R,6aR)-Δ10-THC and (9S,6aR)-Δ10-THC, as starting material that isomerized in toluene-p-sulphonic acid in benzene to lead to (R)-(+)-Δ6a10a-THC and (S)-(−)-Δ6a10a-THC, respectively. More recently, Rosati et al. developed a one-pot microwave assisted synthesis of (R)-(+)-→6a10a-THC and (S)-(−)-Δ6a10a-THC starting from single enantiomers of pulegone condensed with olivetol under Ytterbium triflate-ascorbic acid catalysis. Δ6a10a-THC may be a viable "cutting" agent, which can thicken and dilute concentrated *cannabis* or hemp extract without adding psychoactivity or other ill physical effects. Use of Δ6a10a-THC as a cutting agent for CBD products may also be viable as Δ6a10a-THC is not currently identified by any known state or federal testing hemp laboratory.

Given the potential medicinal value of cannabinoids, improved methods of converting CBD and Δ8-THC to Δ6a10a-THC are needed.

SUMMARY OF THE INVENTION

A method and product are disclosed for converting CBD to Δ8-THC and optionally to Δ9-THC and optionally to Δ10-THC and optionally to 6a10a-THC comprising:
1. Adding an acidic reagent such as p-toluenesulfonic acid monohydrate to pure CBD.
2. Heating the mixture to produce Δ8-THC and Δ9-THC.
3. Optionally adding a secondary catalyst such as sulfur to produce Δ10-THC which is then converted to Δ6a10a-THC by an acidic reagent.

Varying the heat, THC to catalyst ratio, and the atmospheric conditions may result in the acceleration or deceleration of intended reactions and/or side reactions.

DETAILED DESCRIPTION

Figure 1:
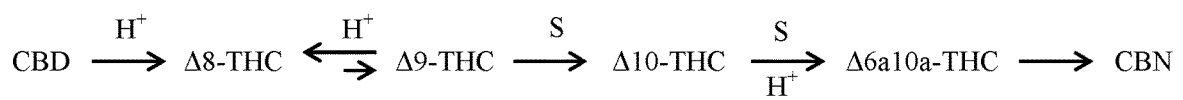
FIG. 1 shows the chemical formula of the general reaction.
Figure 2:
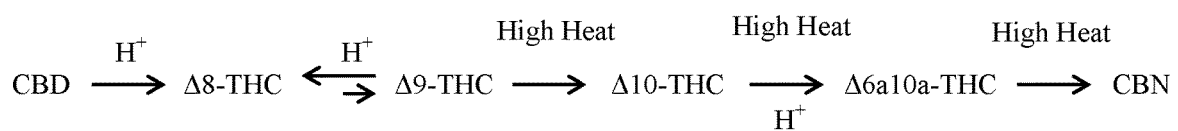
FIG. 2 shows the chemical formula of the general reaction using heat rater than an acidic reagent.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

Described herein are methods and protocols for converting CBD to Δ8-tetrahydrocannabinol (Δ8-THC) and then to Δ6a10a-tetrahydrocannabinol (Δ6a10a-THC). As will be appreciated by one knowledgeable in the art and as discussed below, the reaction times may be varied somewhat, producing product at different yields and purities. Furthermore, functional equivalents may be substituted where appropriate.

In the presence of an acid and a secondary catalyst, Δ6a10-THC and minor amounts of CBN may be produced from CBD or a previously made Δ8-THC. This is not a reported reaction in literature and is previously unknown. It may also be observable that sulfur may be replaceable by extreme heat and time, which, in combination with activated carbons or other conjugate bases of the acids present, provide an appropriate secondary catalyst for initiating conversion of Δ9-THC to Δ10-THC.

The method of converting CBD to Δ8-THC to Δ6a10a-THC and/or cannabinol may be summarized by: heating and mixing a reaction mixture comprising pure CBD or Δ8-THC, an acid, often adding a basic or dehydrogenation catalyst, allowing the mixture to cool; and then, in some embodiments, if desired, purifying reaction products. If desired, the THC may then be combined with suitable excipients known in the art, thereby forming a pharmaceutical composition.

In some embodiments, the acidification may be done through the addition of an acidic catalyst such as p-toluenesulfonic acid monohydrate to the mixture. In other embodiments, acidification may be achieved by leaving residual acids from the acidic conversion process which creates Δ8-THC from CBD or Δ9-THC. Phosphoric acid, citric acid, acidic carbon, and nearly any reagent with documented acidic quality may be used in order to impart acidic quality on the mixture. Some acids may work better under vacuum, some may work best under nitrogen conditions, and others may work fine in atmospheric conditions. Organic solvents may be used if desired.

Acidification of a mixture containing Δ8-THC may be achieved many ways and often, but not always, has an effect on the described reaction. When an acid is used in order to acidify a mixture containing pure CBD, an equilibrium between Δ8-THC and Δ9-THC may be observed after some time under heat. In some cases, this equilibrium reaction may occur at high temperature (citric acid for example) or low temperature (p-toluenesulfonic acid monohydrate). When acidified and heated, a mixture containing CBD may produce an equilibria concentration of Δ9-THC and Δ8-THC, which may then be converted into a mixture of Δ8-THC, Δ9-THC and Δ10-THC through catalysis of Δ9-THC with sulfur or other catalysts. Following the catalytic removal of the Δ9-THC, the acidified mixture may produce an equilibrium concentration of Δ9-THC from Δ8-THC, which in turn may produce more Δ10-THC. The Δ10-THC in the mixture, if the acid present is a strong acid, may be then converted into Δ6a10a-THC with varying yields.

In most embodiments, the second catalyst may be a Lewis base or a hydrogenation/dehydrogenation catalyst such as sulfur. Palladium on carbon may also be a suitable catalyst. The dehydration catalyst may react with the Δ9-THC in the mixture, initiating the reaction which converts it to Δ10-THC and Δ6a10a-THC, depending on temperature. This may occur due to the benzylic and allylic 10 carbon in Δ9-THC, which may lose a hydrogen to the Sulfur, Palladium, or other dehydrogenation catalysts. Δ10-THC may contain a similarly reactive hydrogen which allows sulfur to convert it readily into Δ6a10a-THC. The Δ10-THC created may mainly be the 9R-Δ10-THC isomer rather than 9S-Δ10-THC, which may exist in smaller amounts under these conditions. In described conditions in the examples, small amounts of CBN may also be created but under certain conditions and with some catalysts, these by-products have been minimal. It is expected that a portion of the Δ6a10a-THC produced may contain the 9R stereochemistry. Some conditions may produce a significant amount of the 9S isomer as well. It is also observed that sulfur may likely be unnecessary in order to produce a conversion from Δ10-THC to Δ6a10a-THC and palladium on carbon may facilitate this reaction more completely.

In some embodiments, the material may start as a CBD crystal isolate which is then converted with known methods in the literature to Δ8-THC. An acidic catalyst may be added at a ratio of 20 g Δ8-THC to 0.05 g acid if using p-toluenesulfonic acid, or other amounts for other acids. In other embodiments, p-toluenesulfonic acid may be added at a higher ratio, for example 30 g Δ8-THC to 1 g p-toluenesulfonic acid, however significant losses of cannabinoids may be observed when excess acid is used. In other embodiments insufficient catalyst may be added, for example 30 g Δ8-THC to 0.05 g p-toluenesulfonic acid, which results in a slower conversion of both CBD to Δ8THC and of Δ8THC to Δ6a10aTHC.

In some embodiments, sulfur may be added at a ratio of 30 g Δ8-THC to 0.3 g sulfur. In other embodiments, sulfur may be added at a higher ratio, for example 30 g Δ8-THC to 1 g sulfur. In other embodiments insufficient catalyst may be added, for example 20 g Δ8-THC to 0.1 g sulfur. Insufficient catalyst may result in a decreased reaction rate.

In some embodiments, the temperature may be held above room temperature for a period of time. In some embodiments, the temperature may then be raised or held constant at higher temperatures, which may be 70° C. to 250° C. for some embodiments.

Acid activated carbon, bentonite, or other acid activated powders may be added to a mixture containing CBD without solvent and may result in similar chemistries at around 150° C. to 200° C.

In some embodiments the process may be carried out under a reactive atmosphere which contains oxygen. In other embodiments the process may be carried out under an inert gas atmosphere or vacuum.

Yield and purity may be determined by looking at the peak area for the isolated compound in the liquid chromatography—PDA analysis of the crude reaction product mixture. For especially accurate routine testing, gas chromatography mass spectrometry may also be used.

According to the invention, a method is provided for converting CBD or Δ8-THC to Δ6a10a-THC possibly with a minor product of CBN.

Some target reactions and side reactions that may be observed are listed below:

The first process may be to convert CBD to Δ8-THC and Δ9-THC:

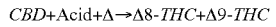

Cleanup may then be performed to remove all or a portion of the acid, or reaction may proceed to General Reaction 1 without cleanup.

General Reaction 1: This reaction may be enhanced by the addition of a carbon powder.

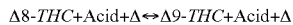
Δ8-*THC*+Acid+Δ↔Δ9-*THC*+Acid+Δ

General Reaction 2: This reaction may be enhanced by the addition of a carbon powder.

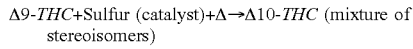
Δ9-*THC*+Sulfur (catalyst)+Δ→Δ10-*THC* (mixture of stereoisomers)

General Reaction 3: This reaction may be enhanced by the addition of a carbon powder.

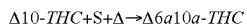
Δ10-*THC*+S+Δ→Δ6a10a-*THC*

Δ10-*THC*+Acid+Δ→Δ6a10a-*THC*

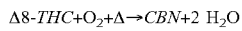
Δ8-*THC*+O$_2$+Δ→*CBN*+2 H$_2$O　　　　Side Reaction 1:

Δ10-*THC*+O$_2$+Δ→*CBN*+2 H$_2$O　　　Side Reaction 2:

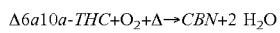
Δ6a10a-*THC*+O$_2$+Δ→*CBN*+2 H$_2$O　　Side Reaction 3:

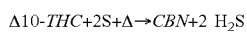
Δ10-*THC*+2S+Δ→*CBN*+2 H$_2$S　　　　Side Reaction 4:

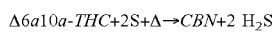
Δ6a10a-*THC*+2S+Δ→*CBN*+2 H$_2$S　　　Side Reaction 5:

When temperature is increased all reactions may increase in rate.

Δ8-THC is commonly produced from combining an acid with CBD. The residual acid of that reaction may substitute for the addition of an acid as described in the present invention. It is expected that the present invention may be practiced by combining CBD with an acid and a catalyst. It is expected that Δ8-THC will be produced which will then react with the residual acid and catalyst to form Δ6a10a-THC and possibly, a minor product of CBN. Following the establishment of an equilibrium reaction, where Δ9-THC may be maintained at low level, sulfur causes the conversion of Δ9-THC to mainly Δ10-THC, which is also maintained at a low level, and which is then converted into increasing amounts Δ6a10a-THC by the said acid.

It is also expected that the present invention may be practiced by combining Δ9-THC with an acid and catalyst. In this case a portion of the Δ9-THC is expected to convert via the catalyst to Δ10-THC. Then the acid converts the Δ10-THC to Δ6a10a-THC. There is also generally a large side product of Δ8-THC depending on the acid used, due to the conversion of Δ9-THC to Δ8-THC.

Example 1: Conversion of Δ8-THC to Δ6a10a-THC and CBN with a Δ9-THC, and Δ10-THC Intermediate Using p-Toluenesulfonic Acid Monohydrate and Sulfur Under Inert Gas Atmosphere In the this example 100 g of CBD (90%, 27 g CBD, 0.085 moles) is converted to a mixture of Δ8-THC (75%, 75 g, 0.24 moles) and Δ9-THC (2.0%, 2.0 g, 0.0063 moles) using around 1% p-toluenesulfonic acid at 60° C. to 90° C. for 8 hours. The reaction was then cleaned with 1% saline washes and potassium carbonate base according to literature. The organic solvent was then recovered. In this example, General Reaction 1, 2 and 3 along with Side Reaction 4 and 5 are observable, although Side Reactions 1, 2 and 3 may be minimized through use of an oxygen-free atmosphere and Side Reactions 4 and 5 may be minimized through use of small amounts of sulfur, which encourages sulfur to function as a catalyst rather than a reactant. A ratio of 12.5 grams of the Δ8-THC-rich oil (75% pure, 9.375 grams Δ8-THC, 29.7 mmol Δ8-THC) to 0.112 g (3 mmol) elemental sulfur pellets and 0.047 g p-toluenesulfonic acid monohydrate was used, although Δ8-THC concentration and catalyst concentration may vary. The cannabinoid mixture contained about 1.8% Δ9-THC initially and 0% Δ10-THC initially, and initially contained 0.8% CBN. In this example, catalyst was added at room temperature and the mixture temperature was increased to 180° C. under an inert nitrogen atmosphere, though argon or any inert gas or vacuum may be used. Heat was maintained at 180° C. under nitrogen for 30 minutes. After 25 minutes, temperature reached 150° C. and Δ8-THC concentration had been maintained at 75.3%, Δ9-THC was maintained at around 2%, with generation of 0% Δ6a10a-THC and 0.8% CBN. After 20 more minutes mixture temperature raised to 160° C. and Δ8-THC concentration had reduced to 53.8%, Δ9-THC was maintained at 1.4%, with generation of 7% Δ6a10a-THC and 1.1% CBN. After 10 more minutes the mixture reached 180° C. and the Δ8-THC concentration reduced to 52%. At this point there was a generation of 8.3% Δ6a10a-THC and 1.2% CBN. After 10 minutes at 180° C., Δ8-THC concentration had reduced to 48.3%, Δ9-THC was maintained at 1.4%, with generation of 11.0% Δ6a10a-THC and 1.8% CBN. After 10 more minutes at 180° C. (20 minutes total at 180° C.), Δ8-THC concentration reduced to 41.9% with generation of 11.3% Δ6a10a-THC and 2.1% CBN. After 30 minutes at 180° C., Δ8-THC concentration reduced to 39% with generation of 14% Δ6a10a-THC and 2.2% CBN. Δ9-THC was maintained at about 1% throughout the reaction. Δ10-THC was also maintained at about 1% throughout the reaction after initiation. Product yields may vary and adjusting the time under heat or the specific temperature of reaction may produce a higher yield of Δ6a10a-THC.

Example 2: Conversion of CBD to Δ6a10a-THC and CBN with a Δ8-THC, Δ9-THC, and Δ10-THC Intermediate Using Phosphoric Acid and Sulfur in an Inert Gas Atmosphere In the second example CBD, was reacted through use of phosphoric acid, sulfur, and heat. In this example, General Reaction 1, 2 and 3 are observed. Side Reactions 1, 2 and 3 may be minimized through use of an oxygen-free atmosphere and Side Reactions 4 and 5 may be minimized through use of small amounts of sulfur, which encourages Δ9-THC to isomerize to Δ10-THC. The Δ10-THC produced is then converted quickly into Δ6a10a-THC by the acid present. The acid used in this example was phosphoric acid though citric acid, p-toluenesulfonic acid, hydrochloric acid and others are suitable. A ratio of 22.5 g of the CBD crystal (90% pure, 20.25 grams CBD, 0.064 moles CBD) to 0.5 g phosphoric acid and 0.202 g sulfur was used, although CBD concentration and catalyst concentration may vary. The cannabinoid mixture contained only CBD initially. In this example, catalysts were added at room temperature and the mixture temperature was increased to 180° C. under an inert nitrogen atmosphere, though argon or any inert gas or vacuum may be used. Heat was maintained at 180° C. under nitrogen for 30 minutes. After 30 minutes at 180° C., CBD concentration reduced to 0.00%. The concentration of Δ8-THC was 40.3%, the concentration of Δ9-THC was 1.9%, the concentration of Δ10-THC was less than 1%, and the concentration of concentration of Δ6a10a-THC was 16.8%. CBN concentration was 2%. Product yields may vary and adjusting the time under heat or the specific temperature of reaction may produce a higher yield of Δ6a10a-THC.

Example 3: Conversion of Δ9-THC to Δ6a10a-THC and CBN with a Δ9-THC Using Sulfur and Acid In the third example, 13.5 g of an oil containing Δ9-THC (81.2%, 10.9 g, 0.035 mole) was reacted through use of an acid, sulfur, heat, and inert atmosphere. In this example, General Reaction 2 and 3 along with Side Reaction 4 and 5 are observable. Side Reactions 1, 2 and 3 may be minimized through use of an oxygen-free atmosphere and Side Reactions 4 and 5 may be minimized through use of small amounts sulfur, which encourages Δ9-THC to isomerize to MO-THC. The acid used in this example was p-toluenesulfonic acid though citric acid, p-phosphoric acid, hydrochloric acid and others are suitable. To the 13.5 g of Δ9-THC oil, 0.05 g p-toluenesulfonic acid and 0.10 g sulfur was used, although Δ9-THC concentration and catalyst concentration may vary. The catalyst may also be added step-wise where the Δ9-THC is converted to Δ10-THC and then acid is used to convert Δ10-THC to Δ6a10a-THC. In this case the cannabinoid mixture contained only Δ9-THC initially. In this example, both the acid and sulfur catalyst were added at room temperature and the mixture temperature was increased to 180° C. under an inert nitrogen atmosphere, though argon or any inert gas or vacuum may be used. Heat was maintained at 180° C. under nitrogen for 30 minutes. After 30 minutes at 180° C., Δ9-THC concentration reduced to 1.3% Δ9-THC. The concentration of Δ8-THC was 51.6%, the concentration of Δ10-THC was less than 1%, and the concentration of concentration of Δ6a10a-THC was 12.0%. Product yields may vary and adjusting the time under heat or the specific temperature of reaction may produce a higher yield of Δ6a10a-THC.

Example 4: Conversion of CBD to Δ8-THC to Δ6a10a-THC and CBN Using Only an Acid and High Heat In the fourth example CBD was reacted through use of phosphoric acid, carbon, and heat. In addition to heat, carbon may also serve as a catalyst for the conversion of Δ9-THC to MO-THC, though it appears to also mildly catalyze also the conversion of Δ8-THC to Δ9-THC and Δ10-THC to Δ6a10a-THC. In this example, General Reaction 1, 2 and 3 are displayed. Side Reactions 1, 2 and 3 may be minimized through use of an oxygen-free atmosphere and Side Reactions 4 and 5 may be minimized through use of no sulfur. The Δ10-THC produced is then converted quickly into Δ6a10a-THC by the acid present. The acid used in this example was phosphoric acid though citric acid, p-toluenesulfonic acid, hydrochloric acid and others are suitable. A ratio of 17.5 grams of the CBD crystal (90% pure, 15.7 grams CBD, 0.05 moles CBD) to 1 g phosphoric acid and 1 g neutral carbon was used, although CBD concentration and catalyst concentration may vary. The cannabinoid mixture contained only CBD initially. In this example, catalyst was added at room temperature and the mixture temperature was increased to 180° C. under an inert nitrogen atmosphere, though argon or any inert gas or vacuum may be used. Heat was maintained at 180° C. under nitrogen for 30 minutes. After 30 minutes at 180° C., CBD concentration reduced to 0% CBD. The concentration of Δ8-THC was 66.5%, the concentration of Δ9-THC was 4.2%, the concentration of Δ10-THC was less than 1%, and the concentration of concentration of Δ6a10a-THC was 3.2%.

The invention claimed is:

1. A process for the conversion of CBD to Δ6a10a-THC.
2. A process for the conversion of Δ8-THC-to Δ6a10a-THC.
3. The process according to claim 1, further using an acidic reagent, a catalyst, and heat.
4. The process according to claim 2, further using an acidic reagent, a catalyst, and heat.
5. The process according to claim 1, further using an acidic reagent and heat.
6. The process according to claim 2, further using an acidic reagent and heat.
7. The process according to claim 5, wherein the acidic reagent is one of phosphoric acid, toluene sulfuric acid, citric acid, acidic bentonite, or acidic carbon.
8. The process according to claim 7, wherein the reactants are heated between 60° C. and 300° C.
9. The process of claim 1, further using heat, an oxidizing agent, and an acidic reagent.
10. The process according to claim 9, wherein the oxidizing agent is elemental sulfur.
11. The process according to claim 10, wherein the acidic reagent is one of phosphoric acid, p-toluene sulfuric acid, citric acid, acidic bentonite, or acidic carbon.
12. The process according to claim 11, wherein the reactants are heated between 60° C. and 300° C.
13. The process according to claim 6, wherein the acidic reagent is one of phosphoric acid, p-toluene sulfuric acid, citric acid, acidic bentonite, or acidic carbon.
14. The process according to claim 13, wherein the reactants are heated between 60° C. and 300° C.
15. The process of claim 2, further using heat, an oxidizing agent, and an acidic reagent.
16. The process according to claim 15, wherein the oxidizing agent is elemental sulfur.
17. The process according to claim 16, wherein the acidic reagent is one of phosphoric acid, p-toluene sulfuric acid, citric acid, acidic bentonite, or acidic carbon.
18. The process according to claim 17, wherein the reactants are heated between 60° C. and 300° C.
19. The process according to claim 3, wherein the catalyst is palladium on carbon.
20. The process according to claim 4, wherein the catalyst is palladium on carbon.

* * * * *